United States Patent [19]

Doherty

[11] 4,144,458

[45] Mar. 13, 1979

[54] SMOKE DETECTOR WITH TEST MEANS FOR SIMULATING A PREDETERMINED CONCENTRATION OF SMOKE

[75] Inventor: William F. Doherty, Halifax, Mass.

[73] Assignee: Chloride Incorporated, Tampa, Fla.

[21] Appl. No.: 855,623

[22] Filed: Nov. 29, 1977

[51] Int. Cl.² .............................................. G01N 21/26
[52] U.S. Cl. ..................................... 250/574; 340/515
[58] Field of Search ................ 340/515, 630; 250/573, 250/574, 575; 356/208

[56] References Cited

U.S. PATENT DOCUMENTS

| 3,868,184 | 2/1975 | Marsocci | 250/574 |
| 4,053,785 | 10/1977 | Lee et al. | 340/515 |

Primary Examiner—David C. Nelms
Attorney, Agent, or Firm—Robert E. Ross

[57] ABSTRACT

A smoke detector of the photo-electric type having a photo-responsive device viewing a volume illuminated by a light beam, in which a test member is provided for being temporarily positioned in the light beam so that one side of said member is exposed to the light and the other side is in the view of the photo-responsive device.

The test member has an area near the forward edge which is thin in relation to the thickness of the rest of the test member. In one embodiment of the invention this area is thin enough to be translucent, so that the translucent area illuminated by the beam simulates a predetermined percentage of smoke in the beam with a high degree of accuracy, since the transmission characteristics of the translucent area can be consistently maintained within production tolerances, and the exact position of the translucent area in the light beam for the smoke simulation is not critical. In another embodiment of the invention, the thin area may or may not be translucent, and a small hole is provided therein extending completely through the thin area to pass a predetermined amount of light from one side of the thin area to the other.

6 Claims, 9 Drawing Figures

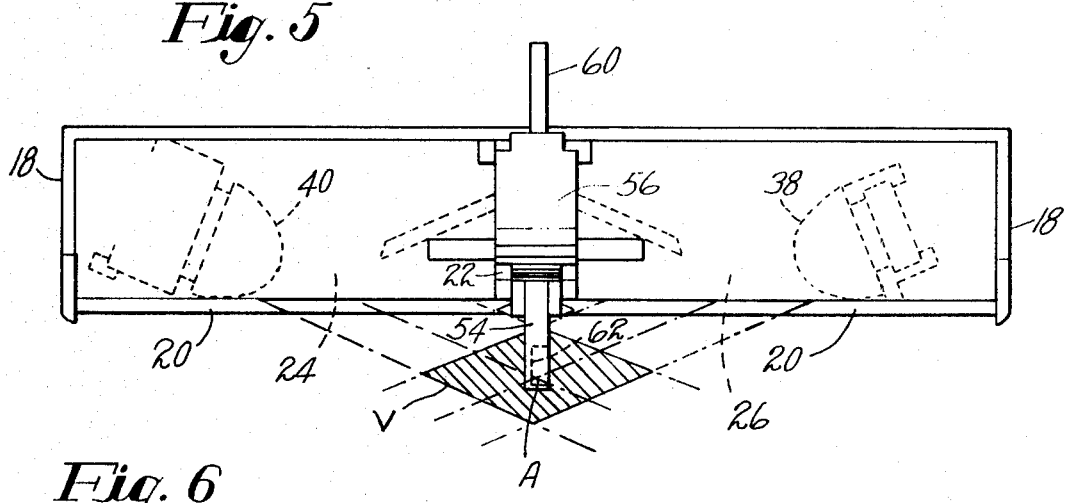
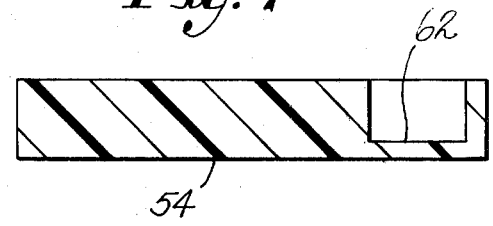
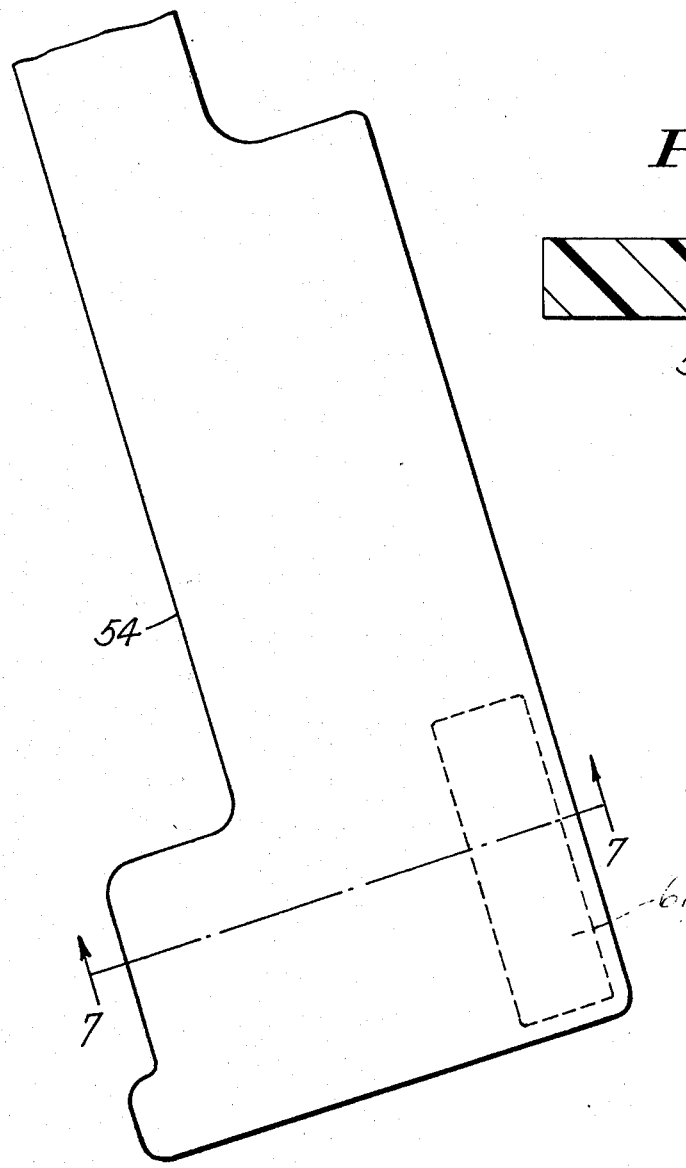

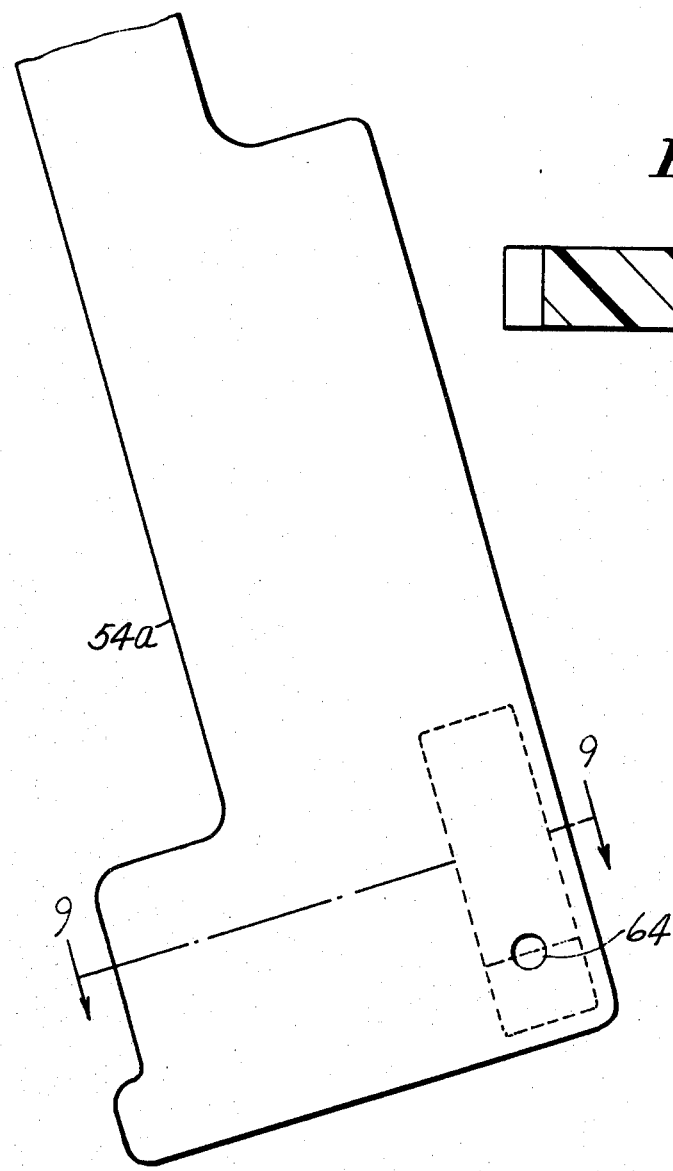
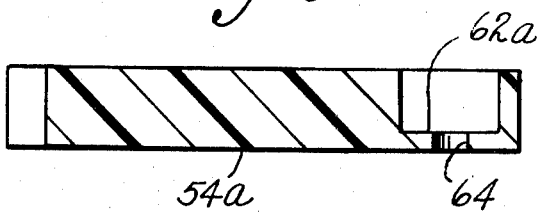
Fig. 8
Fig. 9

SMOKE DETECTOR WITH TEST MEANS FOR SIMULATING A PREDETERMINED CONCENTRATION OF SMOKE

BACKGROUND OF THE INVENTION

Smoke detectors of the photo-electric type utilize a focused light beam passing through a volume which receives smoke from the ambient atmosphere, with a photo-responsive device viewing the light beam at an angle to the axis thereof, so that smoke particles illuminated by the beam are seen by the photo-responsive device.

Such detectors are calibrated to provide an alarm when the concentration of smoke in the light beam reaches a predetermined level. Certain organizations that test and approve smoke detectors require that means be provided whereby the user of the detector can test the operability thereof, by simulating the amount of smoke to which the detector is required to respond.

Various methods have been proposed to provide such test means. However, it has been found difficult to provide a method which will give consistent results in a smoke detector manufactured in great quantity because of the difficulty of holding accurate tolerances in the mechanical components. Methods used heretofore depend on light reflected or scattered from an object, such as a wire, inserted into the light beam. However, the amount of light scattered onto the cell depends on the size of the wire, the surface finish thereof, and its position in the light beam. The diameter of the wire required to provide the small amount of light required is very small, and is therefore susceptible to damage in handling during manufacture or damage in use by the user.

SUMMARY OF THE INVENTION

This invention provides a smoke detector with a test member and means for positioning the test member in the light beam so that one side thereof is illuminated by the light source and the other side thereof is in the view of the photo-responsive device. In one embodiment of the invention a portion of the test member near the front edge thereof is sufficiently thin to be translucent, said translucent portion being small in area in relation to the cross-sectional area of the portion of the light beam into which it is inserted.

In another embodiment of the invention, the thin area may or may not be translucent, and a small hole is provided through said thin area so that a predetermined amount of light passes through the test member when the test member is moved into the light beam.

In one embodiment of the invention, the test member is in the form of a plate positioned in a slot in the housing containing the light source and photocell, and an external lever is provided to move the test plate out of the slot so that the leading edge of the test member enters the light beam. The thin portion is disposed near the leading edge of the test member so as to be centrally disposed both in the light beam and in the field of view of the photo-cell when moved into the test position.

Hence, when the test member is projected forwardly into the light beam, the amount of illumination passing through the test member and seen by the photocell will be consistent from one detector to another so long as the thin portion of the test member is positioned within about the center one quarter of the light beam. The dimensional tolerances of the mechanical components necessary to position the test member in the test position are therefore not restrictive.

BRIEF DESCRIPTION OF THE DRAWINGS

FIG. 5 is a top plan view of FIG. 4.

FIG. 6 is an enlarged view of the test member as seen in FIG. 4.

FIG. 7 is a view in section taken on line 7—7 of FIG. 6.

FIG. 8 is a view similar to FIG. 6, illustrating a modified form of test member.

FIG. 9 is a view taken on line 9—9 of FIG. 8.

DESCRIPTION OF THE ILLUSTRATED EMBODIMENT

Figure 1:
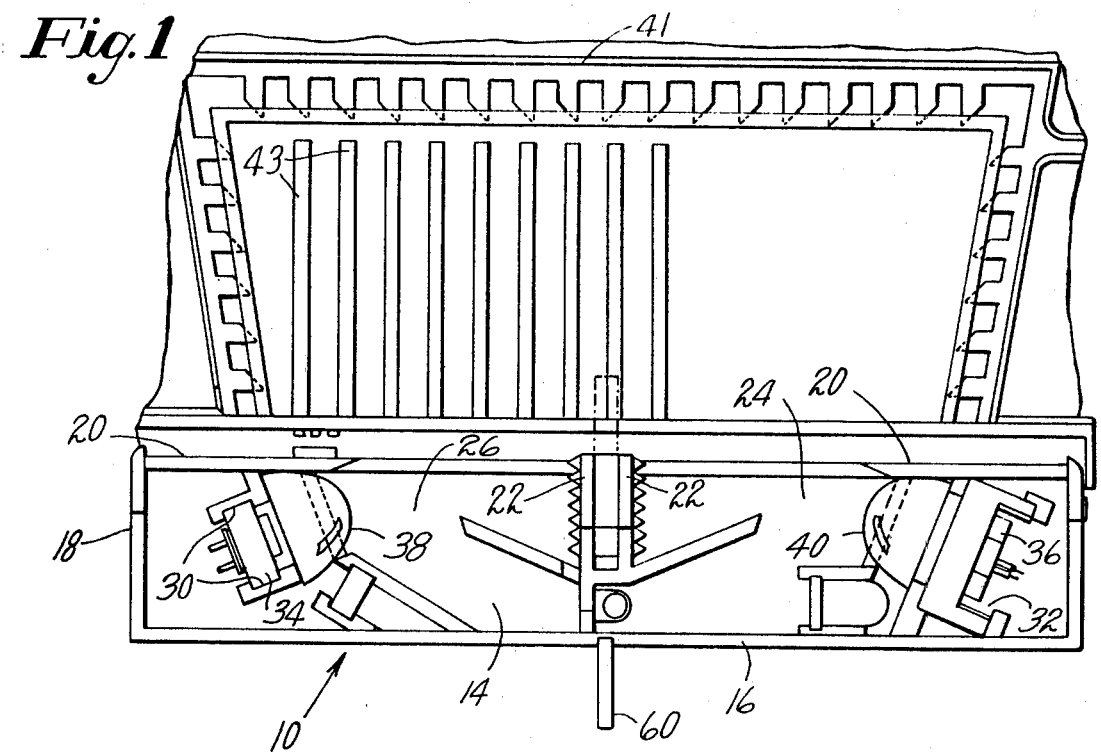
FIG. 1 is a top plan view, partly broken away, showing a housing for the optical components of a smoke detector with the cover removed.
Figure 2:
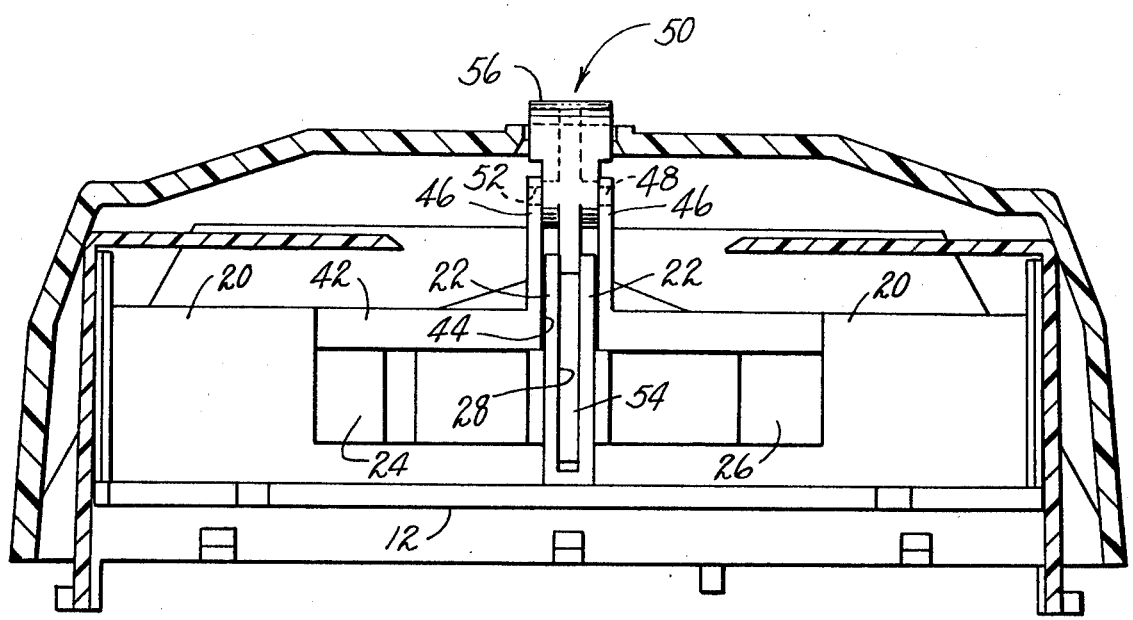
FIG. 2 is a view of the housing of FIG. 1 as seen from the front, with the cover in place.

Referring to the drawing, there is illustrated a housing 10 for use in a smoke detector of the photo-electric type. The housing is preferably formed of injection molded plastic and comprises a body 12 comprising a base 14, a back wall 16, end walls 18, front wall portions 20 and a pair of upstanding members 22 medially disposed between the ends of the front wall portions, forming openings 24 and 26. The upstanding members 22 are spaced apart forming a slot 28.

Other upwardly extending members are provided in the housing to form suitably shaped cavities 30 and 32 to receive a light source 34 and a photoresponsive device 36, with associated focusing lenses 38 and 40.

The cavities 30 and 32 are shaped and dimensioned to retain the light source and photo-responsive device in a position and orientation such that the light beam from the source projects out of the opening 26 at an angle of about 22½° from the longitudinal axis of the housing and the viewing axis of the photo-responsive device extends out of the opening 24 also at an angle of about 22½° to the axis of the housing, so that the viewing axis of the photo-responsive device intersects the axis of the light beam in front of the medial portion of the housing at a point A (FIG. 5) at an angle of about 135° to take advantage of the well-known "forward scatter" effect. The intersection of the viewing cone of the photo-cell and the cone of the light beam is illustrated by the shaded area V.

The light source and photo-responsive device may be connected into suitable circuitry (not shown), by which the light source is energized in a desired manner, and light reflected onto the photo-responsive device from smoke particles in the light beam cause a response of said photo-responsive device that actuates an alarm.

Examples of such circuitry may be found in U.S. Pat. Nos. 3,946,241 issued Mar. 23, 1976, 3,917,956 issued Nov. 4, 1975, and U.S. application Ser. No. 815,103 filed July 13, 1977.

The viewing area of the photo-cell may be surrounded by a suitable enclosure 41 having internal light absorbing baffles 43, said enclosure having suitable apertures (not shown) to freely admit ambient atmosphere.

A cover plate 42 is provided for the housing, said plate being provided with an aperture 44 in the medial portion of the front edge and a pair of support arms 46 extending upwardly on opposite sides of the aperture, each leg having an inwardly extending pin 48 near the upper end thereof.

Figure 3:
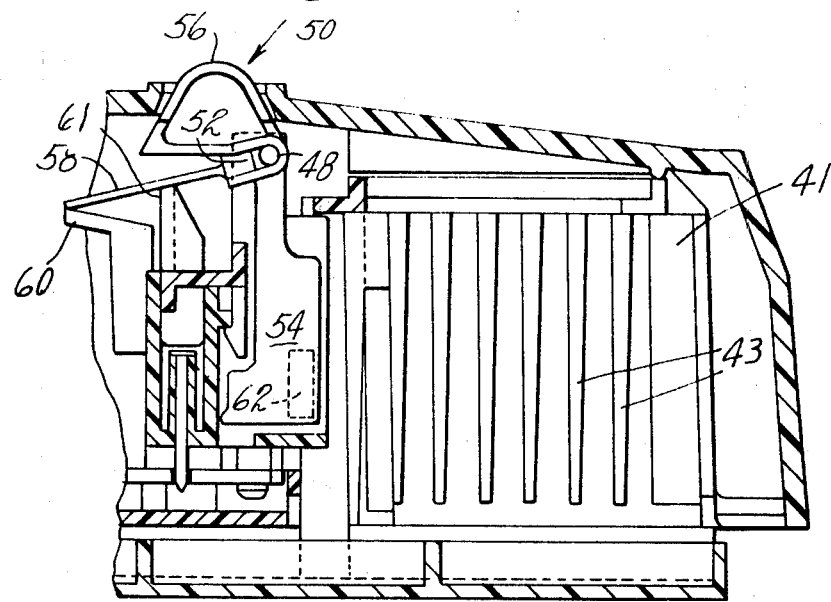
FIG. 3 is a view in section taken on line 3—3 of FIG. 2, with the test member in the normal retracted position.

Assembled with the cover is a test lever 50, comprising a medial portion having a pair of recesses 52 on opposite sides thereof receiving the pins 48 so that the lever is movable on said pins as an axis. Depending from the medial portion is a test plate 54 which is disposed in the slot 28 of the housing, and extending upwardly and rearwardly therefrom is an operating member 56. Extending rearwardly from the lever 50 is an integral plastic leaf spring 58, which, when the lever and cover are assembled with the housing, rests on a spring support 60 on the rear of the housing, so that the lever is biased clockwise (as seen in FIG. 3) retaining the test plate 54 retracted into the slot 28.

Figure 4:
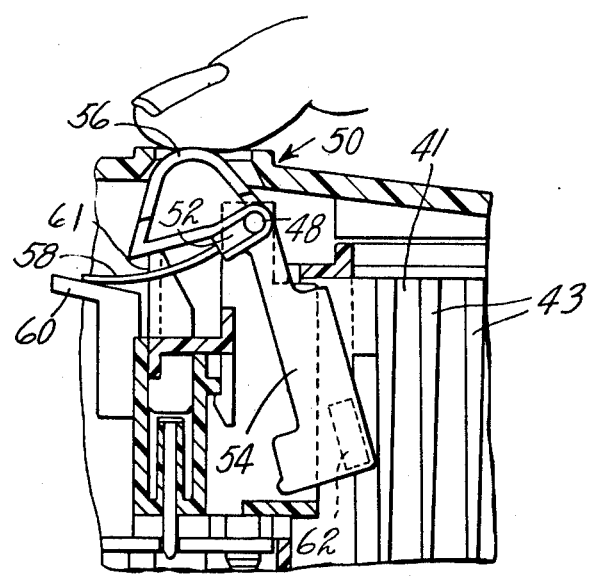
FIG. 4 is a view similar to FIG. 3 in which the test member is in the forward or test position.

The test plate 54 is moved to the test position by depressing the operating member 56, thereby pivoting the lever 50 counter-clockwise (FIG. 4) and flexing the spring 58.

To limit the pivoting movement of the lever, so that when the operating member is depressed the leading edge of the test plate stops substantially at the center of the light beam, stop member 61 is provided on the cover, positioned to contact the operating member 56 and limit the downward movement thereof.

As illustrated in FIGS. 6 and 7, the leading portion of the test plate has an area 62 which is thin in relation to rest of the member, said area being substantially smaller than that of the light beam at the intersection of the light beam and the field of view of the photo-cell. When the test plate is moved forwardly into the light beam, one side thereof is illuminated by the light beam, and the other side is viewed by the photo-responsive device. In a preferred embodiment of the invention the housing 10 and the lever 50 are formed of black plastic, to absorb stray radiation and to minimize the transmission of light through the test plate 54.

However, it has been found that if the area 62 of the test plate is made thin enough, sufficient light is transmitted and seen by the photo-responsive device to simulate the required amount of smoke and actuate the alarm.

The amount of light passing through the thin area 62 of the test plate for a given plastic composition, is a function of the thickness of said thin area and the area thereof. For a detector housing of given size and composition, and with a known amount of smoke to be simulated, the area and thickness that will simulate a required amount of smoke can easily be determined by experiment.

In the accompanying drawing, the thickness of the portion 62 as shown in FIG. 7 is not intended to be a representation of the actual thickness necessary for the desired result.

Although in the illustrated embodiment the translucent portion is provided near the leading edge of the test plate, it will be understood that the thin translucent portion could be in a central portion of the test plate, and means provided for projecting the test plate further into or completely across the light beam so that the thin translucent portion is centered in the light beam.

Referring to FIGS. 8 and 9, there is illustrated a modified form of test plate 54a which is similar to test plate 54, with the exception that the portion 62a need not be so thin as to be translucent, and a small aperture 64 is provided in the portion 62a to allow a predetermined amount of light to pass therethrough. The aperture 64 may be so positioned in the portion 62a as to be substantially centrally located in the light beam when the test plate is in the test position.

Although in the embodiment of FIGS. 8 and 9, the aperture 64 is positioned in a thin portion 62a, it will be understood that if desired the plate may be of uniform thickness with the aperture suitably positioned in the plate. However, the providing of such a small hole in a plate of any appreciable thickness may be a more difficult molding process, and therefore it is preferred to provide a plate of sufficient thickness to impart the necessary strength for handling in bulk after molding and individually after molding, and provide a thin portion in which the aperture is molded, said thin portion being spaced inwardly from the edges of the plate, so that it is protected from damage by the surrounding thicker portion of the plate.

Since changes apparent to one skilled in the art could be made in the illustrated embodiment of the invention without departing from the scope thereof, it is intended that all matter contained herein be interpreted in an illustrative and not a limiting sense.

I claim:

1. In a smoke detector of the photo-electric type which includes a light source providing a light beam and photo-responsive means viewing transversely a portion of the light beam, the improvement comprising test means for simulating a predetermined smoke concentration, said means comprising a substantially opague plate and means for temporarily positioning the plate in the light beam between the light source and the photo-responsive device so that the plate is illuminated on one side by the light beam and the other side is viewed by the photo-responsive device, said plate having a light transmitting portion spaced from the edges thereof, said light transmitting portion allowing a predetermined amount of light to pass therethrough when the plate is so positioned in the light beam.

2. A smoke detector as set out in claim 1 in which said light transmitting portion has an area substantially smaller that the area of the light beam at its intersection with the field of view of the photo-responsive device, and means is provided for positioning said portion substantially in the medial portion of the light beam at the intersection of the light beam with the field of view of the photo-responsive device.

3. A smoke detector as set out in claim 1 in which said light-transmitting portion has a thickness such that it is sufficiently translucent to allow the required amount of light to be seen by the photo-responsive device.

4. A smoke detector as set out in claim 1 in which said light transmitting portion is an aperture.

5. A smoke detector as set out in claim 4 in which said aperture is disposed in a portion of the plate which is substantially thinner than the surrounding portion of the plate.

6. In a smoke detector of the photo-electric type which includes a light source providing a light beam and photo-responsive means viewing transversely a portion of the light beam, the improvement comprising test means for simulating a predetermined smoke concentration, said means comprising a substantially opague plate temporarily movable into a position at the intersection of the field of view of the photo-responsive device and the light beam and light transmitting means formed in the plate, said light transmitting means being substantially smaller in area than the area of the light beam at said intersection, said light transmitting means being in a portion of the plate which is substantially thinner than the surrounding portion of the plate.

* * * * *